United States Patent [19]

Rizzardo et al.

[11] Patent Number: 5,773,543

[45] Date of Patent: Jun. 30, 1998

[54] ALLYLIC CHAIN TRANSFER AGENTS

[75] Inventors: Ezio Rizzardo, Wheelers Hill; San Hoa Thang, Clayton South; Graeme Moad, Kallista, all of Australia; Charles Thomas Berge, Wilmington, Del.

[73] Assignee: Commonwealth Scientific and Industrial Research Organisation, Campbell, Australia

[21] Appl. No.: 635,907

[22] PCT Filed: Nov. 2, 1994

[86] PCT No.: PCT/AU94/00672

§ 371 Date: Aug. 1, 1996

§ 102(e) Date: Aug. 1, 1996

[87] PCT Pub. No.: WO95/12568

PCT Pub. Date: May 11, 1995

[30] Foreign Application Priority Data

Nov. 3, 1993 [AU] Australia ................................. PM2188

[51] Int. Cl.[6] ...................................................... C08F 2/38
[52] U.S. Cl. ............................. 526/215; 526/78; 526/79; 526/82; 526/83; 526/84; 526/209; 526/213; 526/214; 526/216; 526/217; 560/129; 560/155; 560/170
[58] Field of Search ..................................... 526/213, 214, 526/215, 78, 79, 82, 83, 84, 209, 216, 217; 560/129, 155, 170

[56] References Cited

U.S. PATENT DOCUMENTS

| 3,707,529 | 12/1972 | Gladding . | |
|---|---|---|---|
| 3,839,309 | 10/1974 | Moore . | |
| 4,032,699 | 6/1977 | West, III | 526/18 |
| 4,124,753 | 11/1978 | Dench | 526/208 |
| 4,322,491 | 3/1982 | Sander et al. | 430/286 |
| 4,503,207 | 3/1985 | Heyman | 526/307.5 |
| 4,524,197 | 6/1985 | Khan | 526/206 |
| 4,692,493 | 9/1987 | Sulzbach et al. | 524/805 |
| 4,753,981 | 6/1988 | Clark, Jr. | 524/801 |
| 5,010,189 | 4/1991 | Herold et al. | 544/174 |
| 5,208,305 | 5/1993 | Grootaerj | 526/194 |
| 5,260,392 | 11/1993 | Arcella | 526/247 |
| 5,264,530 | 11/1993 | Darmon | 526/194 |
| 5,362,826 | 11/1994 | Berge | 526/194 |
| 5,385,996 | 1/1995 | Rizzardo et al. | 526/240 |

FOREIGN PATENT DOCUMENTS

| B191457/76 | 7/1979 | Australia . |
|---|---|---|
| B-83396/87 | 4/1987 | Australia . |
| 1 556 999 | 12/1979 | European Pat. Off. . |
| 52-111509A | 9/1977 | Japan . |
| WO91/06535 | 5/1991 | WIPO . |
| WO 93/22355 | 11/1993 | WIPO . |

OTHER PUBLICATIONS

J. March, "Advanced Organic Chemistry," 4th Ed. (1992), 465, Wiley (New York).

Sumitomo Kagaku Kogyo K.K., Patent Abstracts of Japan (Abstract, formula (III)), JP,A, 52–111509, C–77, 3813, 19 Sep. 1997.

Takashi Tsuda and Lon J. Mathias, New Dicyano–Containing Cyclopolymers Having High Stereoregularity Derived from Dimethacrylmalononitrile, *Macmomolecules*, 26, 6359–6363, 1993.

International Search Report, International Application No. PCT/AU94/00672, Feb. 10, 1995.

*Primary Examiner*—Fred Zitomer

[57] ABSTRACT

A process for the free radical initiated polymerization of unsaturated species characterized by the use of compound of Formula (I) as chain transfer agents:

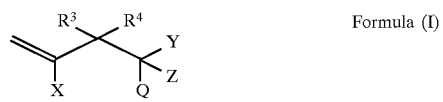

Formula (I)

wherein:

X is selected from hydrogen; CN; optionally substituted aryl; COOH; COOR; C(O)NHR[6]; C(O)NR[7]R[8]; and halogen;

Q is selected from COOR[1]; CN; and C(O)NR[7]R[8];

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN and optionally substituted aryl; $C_1$ to $C_6$ alkenyl; and $C_1$ to $C_6$ alkynyl;

Z is selected from COOR[2]; CN; and optionally substituted aryl;

R[3] and R[4] are the same or different and are selected from hydrogen $C_1$ to $C_4$ alkyl and halogen; or R[3] and R[4] together with carbon atom to which they are attached form part of a carbocyclic or heterocyclic ring structure; and the other substituents are as defined in the text.

17 Claims, No Drawings

ALLYLIC CHAIN TRANSFER AGENTS

This invention relates to processes for radical-initiated polymerization of unsaturated species and for the control of molecular weight of the polymers produced from such processes. Polymers of low molecule weight, or oligomers, are important as precursors in producing other polymeric materials and such polymers have been found to be useful in a variety of products, for example, in the production of high solids (low VOC) surface coatings, in adhesives and as plasticizers in polymeric composites.

In conventional polymerization practice, the manufacture of oligomers requires the use of an initiator which acts as a free radical source, and of a chain transfer agent. The chain transfer agent controls the molecular weight of the polymer by reacting with the propagating polymer radical to terminate its growth. It then initiates a new polymer chain thus transferring the growth process from one discrete polymer molecule to another discrete polymer molecule.

The most commonly used chain transfer agents are alkanethiols, which normally are associated with an objectionable odour and lead to a wide distribution of molecular weight with certain monomers. Also, the residual thiols and the end thio-ether linkage of the polymers may have an adverse effect on the properties of the ultimate product from the polymer.

The present invention helps overcome the disadvantages of polymerizations regulated with thiols by using alternative polymerization regulators. These regulars have good stability and shelf life while maintaining many of the advantages over thiols. In the majority of cases, the materials that are part of the present process present a different range of chain transfer activities, allowing more opportunity for an optimal process to be selected for a given polymerization system of monomers and polymerization conditions. The chain transfer constant that a given regulator possesses is an important consideration in selecting the optimum process for producing low molecular weight polymers.

This invention provides a process for the free radical polygon of unsaturated species to provide polymers with lower molecular weight and narrower polydispersity characterised by the use of compounds of Formula (I) as chain transfer agents.

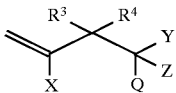

Formula (I)

wherein

X is selected from hydrogen; CN; optionally substituted aryl; COOH; COOR; $C(O)NHR^6$; $C(O)NR^7R^8$; and halogen;

Q is selected from $COOR^1$; CN; and $C(O)NR^7R^8$;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN and optionally substituted aryl; $C_1$ to $C_6$ alkenyl; and $C_1$ to $C_6$ alkynyl;

Z is selected from $COOR^2$; CN; and optionally substituted aryl;

$R^3$ and $R^4$ may be the same or different and are selected from hydrogen, $C_1$ to $C_4$ alkyl and halogen; or $R^3$ and $R^4$ together with the carbon atom to which they are attached form part of a carbocyclic or heterocyclic ring structure;

R is selected from $C_1$ to $C_{18}$ alkyl; $C_1$ to $C_{12}$ alkyl substituted with one or more substituents selected from hydroxy, amino, $C_1$ to $C_6$ alkoxy, phenyl halogen, NCO, CN, and $COOR^5$;

$R^1$ and $R^2$ may be the same or different and are selected from $C_1$ to $C_{18}$ alkyl; $C_1$ to $C_{12}$ alkyl substituted with one or more substituents selected from hydroxy, $C_1$ to $C_6$ acyloxy, $C_1$ to $C_6$ alkoxy, amino, halogen, $Si(R^9)_3$, $Si(OR^9)_3$, optionally substituted aryl, CN and NCO;

$R^5$ is selected from hydrogen and $C_1$ to $C_6$ alkyl;

$R^6$ is selected from hydrogen and $C_1$ to $C_{18}$ alkyl;

$R^7$ and $R^8$ may be the same or different and are selected from $C_1$ to $C_{18}$ alkyl; and $R^9$ is selected from $C_1$ to $C_{18}$ alkyl; $C_1$ to $C_{18}$ cycloalkyl; and optionally substituted aryl.

A preferred group of compounds of Formula I are the malonates with $Q=COOR^1$ and $Z=COOR^2$ having the Formula (IA):

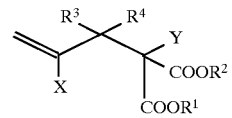

Formula (IA)

wherein:

X is selected from hydrogen; CN; optionally substituted aryl; COOH; COOR; $C(O)NHR^6$; $C(O)NR^7R^8$; and halogen;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN, optionally substituted aryl; $C_1$ to $C_6$ alkenyl; and $C_1$ to $C_6$ alkynyl;

$R^1$ and $R^2$ may be the same or different and are selected from $C_1$ to $C_{18}$ alkyl; $C_1$ to $C_{12}$ alkyl substituted with a substituent selected from hydroxy, $C_1$ to $C_6$ acyloxy, $C_1$ to $C_6$ alkoxy, amino, halogen, optionally substituted aryl, CN and NCO;

$R^3$ and $R^4$ may be the same or different and are selected from hydrogen; $C_1$ to $C_4$ alkyl; and halogen; and R, $R^6$, $R^7$ and $R^8$ are as defined above.

Another preferred group of compounds which possess high chain transfer activities are the compounds of Formula (IB) where $Q=COOR^1$ and Z is optionally substituted aryl:

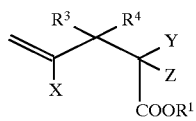

Formula (IB)

wherein:

X Y, $R^1$, $R^3$ and $R^4$ are as defined above; and

Z is optionally substituted aryl.

The term "optionally substituted aryl" is used herein to mean an aromatic carbocyclic group which may or may not be substituted with one or more substituents that do not interfere with the polymerization process. Such substituents include alkyl, hydroxyalkyl, aminoalkyl, carboxylic acid, ester, acyloxy, amide, nitrile, haloalkyl, alkoxy, phosphonate, sulfonate, silyl or silyloxy groups.

Preferred aryl groups are phenyl or naphthyl groups.

When X is halogen, chlorine or bromine are preferred.

When $R^3$ or $R^4$ is halogen, chlorine or fluorine are preferred.

The following compounds of Formula I are novel and form part of the invention:

ethyl 2,4-bis(ethoxycarbonyl)-2-methyl-4-pentenoate;
ethyl 2,4-bis(ethoxycarbonyl)-2-ethyl-4-pentenoate;
ethyl 2-benzyl-2,4-bis(ethoxycarbonyl)-4-pentenoate;
ethyl 2-ethoxycarbonyl-2-methyl-phenyl-4-pentenoate;
ethyl 2-ethoxycarbonyl-2,3-dimethyl-4-(t-butoxycarbonyl)-4-pentenoate; and ethyl 2-phenyl-4-(t-butoxycarbonyl)-4-pentenoate.

The process of this invention uses the compounds of Formula (I) as alternatives to thiols or other chain transfer agents for the control of molecular weight. The process of this invention may be operated in a similar manner to conventional processes using thiols. The compounds of Formula I can be prepared easily from inexpensive starting materials. Unlike thiols, they do not, in general, possess an objectionable odour.

The materials of this invention exhibit unexpectedly good chain transfer activities in general. For example, compound ethyl 2,4-bis(ethoxycarbonyl)-2-methyl-4-pentenoate (Ib) of this invention possesses significantly higher activity when compared with the methyl 4-methoxycarbonyl-2,2-dimethyl-4-pentenoate (MMA dimer or dimethyl 2,2-dimethyl-4-methylene glutarate) (refer to Table 5) in methyl methacrylate, acrylate and styrene polymerizations. The advantages of this invention will become more apparent by referring to the illustrative non-limiting examples shown below.

Preparation of Chain Transfer Agents

The allylic malonate derivatives [Formula (IA)] are synthesized in good to excellent yield in a one-step reaction between the corresponding allylic halides (II) and malonates (IIIA). The reaction is carried out in the presence of base and solvent. Acetonitrile, N,N-dimethylformamide (DMF), dried THF or diethyl ether are suitable solvents. Although many (inorganic and organic) bases are suitable, sodium hydride, sodium alkoxide, sodamide, potassium alkoxides are preferred bases. The use of sodium hydride is found to provide better results than sodium alkoxide for the synthesis of these types of compounds.

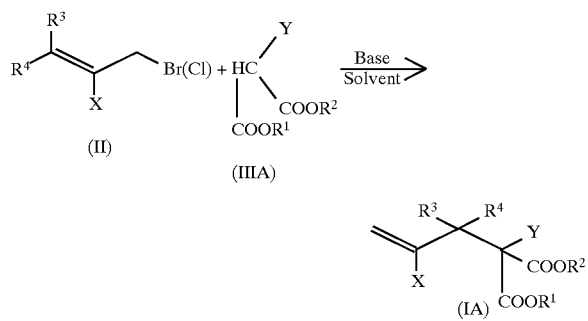

Similarly, the allylic compounds of Formula IB [e.g., compound (Ii)] can be synthesized in good yield in a one-step reaction between the corresponding allylic halide (II) and arylacetate (IIIB). The reaction is carried out in the presence of base and solvent.

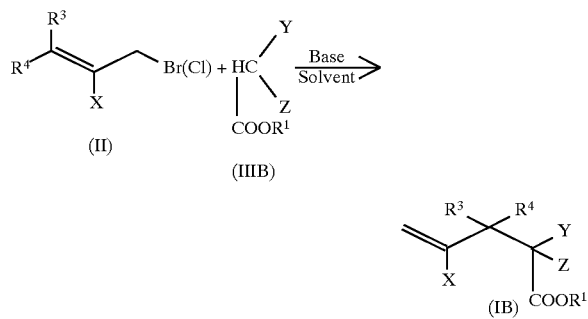

Typical compounds (Ia & Ib) used in the process of this invention and their preparation are further illustrated by the following non-limiting preparative examples.

PREPARATIVE EXAMPLE 1

Ethyl 2,4-bis(ethoxycarbonyl)-4-pentenoate (Ia)
[Formula (IA), X=COOCH$_2$CH$_3$; Y=R$^3$=R$^4$=H; R$^1$=R$^2$=CH$_2$CH$_3$]. [Typical procedure].

To a suspension of sodium hydride (80% dispersion in oil, 0.36 g, 12 mmol) in acetonitrile (10 mL), was added diethyl malonate (1.60 g, 10 mmol). The resulting suspension was allowed to stir at room temperature for 15 minutes. A solution of ethyl α-(bromomethyl)acrylate [obtained from a modified of S. E. Drewes, G. Loizou and G. H. P. Roos, *Synthetic Communications*, 1987, 17(3), 291–298] (1.93 g, 10 mmol) in acetonitrile (5 mL) was then added slowly to the above suspension. Stirring was maintained for 2 hours and then the reaction mixture was poured into water, and extracted (3x) with diethyl ether. The extracts were combined and dried over anhydrous Na$_2$SO$_4$, filtered and evaporated to dryness. Distillation of the crude product under reduced pressure gave (Ia) as a colourless liquid (b.p. ~140° C./0.1 mmHg) (1.90 g, ~70%). $^1$H-NMR (CDCl$_3$) δ(ppm) 1.21 (t, 6H), 1.25 (t, 3H), 2.85 (d, 2H), 3.67 (t, 1H), 4.15 (q, 4H), 4.20 (q, 2H), 5.60 (br. s, 1H) and 6.18 (br. s, 1H). $^{13}$C-NMR (CDCl$_3$) δ(ppm) 13.98, 31.34, 50.76, 60.81, 61.37, 127.56, 136.68, 166.38 and 168.67.

PREPARATIVE EXAMPLE 2

Ethyl 2,4-bis(ethoxycarbonyl)-2-methyl-4-pentenoate (Ib)
[Formula (IA), X=COOCH$_2$CH$_3$; Y=CH$_3$; R$^3$=R$^4$=H; R$^1$=R$^2$=CH$_2$CH$_3$].

This compound was prepared using a similar procedure to that described above. Pure ethyl 2,4-bis(ethoxycarbonyl)-2-methyl-4-pentenoate (Ib) was obtained (60% yield) after column chromatography on silica-gel (diethyl ether: n-hexane 1:4 as eluent). $^1$H-NMR (CDCl$_3$) δ(ppm) 1.20 (t, 6H), 1.25 (t, 3H), 1.33 (s, 3H, 2.95 (s, 2H), 4.15 (m, 6H), 5.56 (br. s, 1H) and 6.22 (br. s, 1H). $^{13}$C-NMR (CDCl$_3$) δ(ppm) 13.91, 14.06, 35.98, 53.88, 60.78, 61.23, 128.61, 136.29, 166.67 and 171.57.

PREPARATIVE EXAMPLE 3

Ethyl 2,4-bis(ethoxycarbonyl)-2-ethyl-4-pentenoate (Ic)
[Formula (IA), X=COOCH$_2$CH$_3$; Y=CH$_2$CH$_3$; R$^3$=R$^4$=H; R$^1$=R$^2$=CH$_2$CH$_3$].

This compound was prepared in ~80% yield using a similar procedure to that described in Example 1. $^1$H-NMR (CDCl$_3$) δ(ppm) 0.85 (t, 3H), 1.20 (t, 6H), 1.30 (t, 3H), 1.85 (q, 2H), 2.95 (s, 2H), 4.15 (m, 6H), 5.58 (br. s, 1H) and 6.25 (br. s, 1H). $^{13}$C-NMR (CDCl$_3$) δ(ppm) 8.58, 14.06, 14.16, 25.46, 32.98, 58.32, 60.89, 61.15, 128.42, 136.53, 167.05 and 171.09.

PREPARATIVE EXAMPLE 4

Ethyl 2-benzyl-2,4-bis(ethoxycarbonyl)-4-pentenoate (Id)
[Formula (IA), X=COOCH$_2$CH$_3$; Y=CH$_2$C$_6$H$_5$; R$^3$=R$^4$=H; R$^1$=R$^2$=CH$_2$CH$_3$].

This compound was prepared by a procedure similar to Example 1, using diethyl benzylmalonate as the starting material; the product was isolated in 76% yield as a colourless syrup. $^1$H-NMR (CDCl$_3$) δ(ppm) 1.20 (t, 6H), 1.30 (t, 3H), 2.95 (s, 2H), 3.25 (s, 2H), 4.15 (m, 6H), 5.65 (br. s, 1H), 6.25 (br. s, 1H) and 7.20 (m, 5H). $^{13}$C-NMR (CDCl$_3$) δ(ppm) 13.82, 14.11, 30.40, 39.63, 43.30, 58.75, 60.84, 61.20, 126.87, 128.11, 128.55, 130.08, 167.40 and 170.56.

PREPARATIVE EXAMPLE 5

Ethyl 4-chloro-2-ethoxycarbonyl-2-methyl-4-pentenoate (Ie)
[Formula (IA), X=Cl; Y=$CH_3$; $R^3$=$R^4$=H; $R^1$=$R^2$=$CH_2CH_3$].

To a suspension of sodium hydride (25.2 g, 0.84 moles, 80% dispersion in oil) and diethyl methylmalonate (104.5 g, 0.60 moles) in acetonitrile (500 mL), a solution of 2,3-dichloropropene (66.6 g, 0.60 moles) in acetonitrile (100 mL) was added slowly over 20 minutes with stirring at room temperature. The resulting mixture was allowed to stir at room temperature overnight. Water (250 mL) was added, and the mixture extracted three times with diethyl ether (200 mL×3). The combined organic layers were washed successively with water (200 mL) and brine (200 mL), they were then dried over anhydrous $MgSO_4$. After removal of the organic solvent, distillation of the crude product under reduced pressure afforded the product (Ie) as a colourless liquid (91.6 g, 61.5% yield), b.p. 77°–78° C. (0.1 mmHg). $^1$H-NMR ($CDCl_3$) δ(ppm) 1.22 (t, 6H), 1.42 (s, 3H), 3.00 (s, 2H), 4.18 (q, 4H), 5.20 (s, 1H) and 5.30 (s, 1H).

PREPARATIVE EXAMPLE 6

Ethyl 2-ethoxycarbonyl-4-phenyl-4-pentenoate (If)
[Formula (IA), X=Phenyl; Y=$R^3$=$R^4$=H; $R^1$=$R^2$=$CH_2CH_3$].

This compound was prepared in ~20% yield (not optimized according to a similar procedure to that described in Example 1. The reaction was carried out between α-(bromomethyl)styrene [obtained from the reaction of α-methylstyrene and N-bromosuccinimide in carbon tetrachloride according to the published procedure by H. Pines, H. Alul and M. Kolobielski, J. Org. Chem., 1957, 22, 1113–1114] and diethyl malonate in the presence of sodium hydride (1 eq.). $^1$H-NMR ($CDCl_3$) δ(ppm) 1.25 (t, 6H), 3.10 (d, 2H), 3.50 (t, 1H), 4.17 (q, 4H), 5.15 (br. s, 1H), 5.35 (br. s, 1H) and 7.35 (m, 5H).

PREPARATIVE EXAMPLE 7

Ethyl 2-ethoxycarbonyl-2-methyl-4-phenyl-4-pentenoate (Ig)
[Formula (IA), X=Phenyl; Y=$CH_3$; $R^3$=$R^4$=H; $R^1$=$R^2$=$CH_2CH_3$].

This compound was prepared in ~60% yield by reacting α-bromomethyl)styrene [obtained by method of H. Pines, H. Alui, M. Kolobielski, J. Org. Chem., p. 1113 (1957)] and diethyl methylmalonate in the presence of sodium hydride (2 eq.) in acetonitrile solvent. $^1$H-NMR ($CDCl_3$) δ(ppm) 1.10 (t, 6H), 1.30 (s, 3H), 3.18 (s, 2H), 3.90 (m, 4H), 5.10 (br. s, 1H), 5.27 (br. s, 1H) and 7.30 (m, 5H).

PREPARATIVE EXAMPLE 8

Ethyl 2-ethoxycarbonyl-2,3-dimethyl-4-(t-butoxycarbonyl)-4-pentenoate (Ih)
[Formula (IA), X=COOC($CH_3$)$_3$; Y=$CH_3$; $R^3$=H; $R^4$=$CH_3$; $R^1$=$R^2$=$CH_2CH_3$].

The starting material, t-butyl (Z)-2-bromomethyl-2-butenoate, was prepared via literature procedures [H. Hoffman and J. Rabe, Helvetica Chimica. Acta, 67(2), p. 413 (1984)].

A stirred solution of diethyl methylmalonate (1.5 g, 8.6 mmol) in distilled THF was cooled to -5° C. and sodium hydride (0.52 g) added portionwise. The resultant suspension was stirred below 0° C. for an hour, then t-butyl (Z)-2-bromomethyl-2-butenoate added dropwise. The mixture was stirred below 0° C. for a further two hours before being allowed to warm to room temperature and stirred overnight Solvent was removed under reduced pressure, water added and the product extracted with ether (3×50 ml), and the combined organic layers dried over anhydrous magnesium sulphate. Upon removal of ether under reduced pressure, a pale yellow oil was obtained (2.02 g, 72%). $^1$H-NMR spectrum revealed the presence of two isomers in a ratio of 4:1, with the preferred isomer being the major product (Ih). Column chromatography on silica gel (9:1, pet. spirit 40°–60° C.: ethyl acetate) gave slight separation of the two isomers. The fraction containing the highest level of ethyl-2-ethoxycarbonyl-2,3-dimethyl-4-(t-butoxycarbonyl) pent-4-enoate (Ih) was used for the following spectroscopic data. $^1$H-NMR ($CDCl_3$) δ(ppm): 6.25, s, 1H; 5.55, s, 1H; 4.2, m, 4H; 3.7, q, 1H; 1.2–1.6, m, 21H. $^{13}$C-NMR ($CDCl_3$) δ(ppm): 171.7, 171.2, 166.6, 143.5, 125.2, 80.5, 61.1, 57.5, 36.7, 28.0, 17.5, 17.0, 14.0, 13.9.

PREPARATIVE EXAMPLE 9

Ethyl 2-phenyl-4-(t-butoxycarbonyl)-4-pentenoate (Ii)
[Formula (IB), X=COOC($CH_3$)$_3$; Y=$R^3$=$R^4$=H; $R^1$=$CH_2CH_3$; Z=phenyl]

The starting allylic bromide material, t-butyl 2-(bromomethyl)propenoate was prepared via a modified procedure of S. E. Drewes, G. Loizou and G. H. P. Roos, Synthetic Communication, 1987, 17(3), 291–298 using t-butyl acrylate.

Ethyl phenylacetate (6.66 g, 40.6 mmol) was dissolved in dry THF (20 mL) and sodium hydride (1.09 g, 36.5 mmol) added portionwise. The resulting suspension was stirred at room temperature for 30 minutes then cooled on ice while t-butyl 2-(bromomethyl)propenoate (4.49 g, 20.3 mmol) was added dropwise under nitrogen atmosphere. On completion of the addition, the reaction mixture was allowed to reach room temperature then heated under reflux for 8 hours. The THF solvent was removed under reduced pressure, water added and the product mixture extracted with diethyl ether (3×50 mL). After removal of organic solvent, the excess ethyl phenylacetate was removed by vacuum distillation and the residue was chromatographed on a silica-gel column using 5% ethyl acetate in petroleum spirit as eluent. The pure product (Ii) was obtained as a very pale yellowish liquid (2.5 g, 41%). $^1$H-NMR ($CDCl_3$) δ(ppm): 1.10, t, 3H; 1.45, s, 9H; 2.65, dd, 1H; 3.00, dd, 1H; 3.85, dd, 1H; 4.10, m, 2H; 5.35, s, 1H; 6.00, s, 1H; 7.25, s, 5H.

Operation of the Process

The process of this invention may be adopted by the users of conventional processes using thiols with little change to reaction conditions other than the substitution of the appropriate quantity of compound of general Formula (1) for the thiol. The proportion of compound of Formula (I) used may be in the range of 0.01 to 30 mole percent based on total monomer, with a preferred range of 0.1 to 10 mole percent The process may be operated at any of the reaction conditions appropriate to free radical polymerization, i.e., temperatures from -100° C. to 200° C. and pressures from below atmospheric to substantially above atmospheric.

The polymerization process can be carried out in bulk, solution, emulsion, mupon or other conventional polymerization modes Source of radicals for polymerizations are well known in the art and they include α,α'-azobisisobutyronitrile, 4,4'-bis(4-cyanovaleric acid), 2,2'-azobis(2,4-dimethylpentanenitrile), benzoyl peroxide, t-butyl peroxybenzoate, ammonium persulfate, potassium persulfate.

Any unsaturated monomers susceptible to free radical polymerization may be used although it should be noted that the chain transfer constant will vary with the monomer used.

Suitable unsaturated monomers include acrylic esters, methacrylic esters, vinyl esters, vinyl aromatics, unsaturated or polyunsaturated hydrocarbons, or mixtures of these. Examples of these monomers are methyl acrylate, ethyl acrylate, butyl acrylate, 2-ethylhexyl acrylate, methyl methacrylate, ethyl methacrylate, n-butyl methacrylate, 2-ethylhexyl methacrylate, vinyl acetate, styrene, p-chloromethylstyrene, 2-vinylpyridine, 4-vinylpyridine, N-vinylpyrrolidone, vinyl halides of the formula $CH_2=CHX$ where X is Cl or F, vinylidene halides of the formula $CH_2=CX_2$ wherein X is independently Cl or F, vinyl ethers $CH_2=CHOR$ where R is alkyl and allyl monomers such as allyl ethers, allyl carbonates or diallyl carbonates.

Compounds of general Formula (I) used in the process of this invention display an unexpected high activity in controlling molecular weight in polymerization reactions and have chain transfer constants that may be superior to those of thiols, particularly with styrene and acrylates. Their activity is such that their chain transfer constants can approach the optimum values of 1.0 for batch polymerizations and this activity is not as highly dependent as that of thiols on the structure of the propagating radical.

The process is applicable to the manufacture of synthetic rubbers, and other polymer formulations where reduced molecular weight aids processing and improves properties. The process can also be used to produce low molecular weight polymers, oligomers, macromonomers and functional polymers for a variety of applications such as high-solids surface coatings, paints, and adhesives. Furthermore, the process can be used to enable better control over the polymerization kinetics, e.g., delaying the onset of gelation in cross-linking systems.

The operation of this process is demonstrated by the following non-limiting examples. In these examples molecular weight measurements were performed on a Waters Associates liquid chromatograph equipped with differential refractometer and six $\mu$-styragel columns of $10^6$, $10^5$, $10^4$, $10^3$, 500 and 100 Å pore size. Tetrahydrofuran solvent was used at a flow rate of 1 mL/min. Results were derived by comparison with polystyrene standards using the Chromatix GPC-1 program.

The conversions were determined from the mass of the polymer isolated after precipitation in solvents where appropriate or after removal of all the volatiles in vacuo, and after subtracting the mass of the chain transfer agent.

EXAMPLE 1

Polymerization of Methyl Methacrylate $\alpha,\alpha'$-Azobisisobutyronitrile (23.4 mg) was dissolved in freshly distilled inhibitor-free methyl methacrylate (MMA) (25 mL). Aliquots (4 mL) were removed and added to ampoules containing weighed amounts of the allylic chain transfer agent of Formula (I). The contents of the ampoule were either degassed by three freeze-evacuate-thaw cycles and sealed under vacuum or by bubbling nitrogen through the solution. The mixtures were then polymerized at 60° C. for one hour. The contents of the ampoules were then added dropwise to methanol and the precipitated polymers were collected and dried in a vacuum oven to constant weight. A small portion of each polymer was examined by gel-permeation chromatography (GPC) to determine its molecular weight.

TABLE 1

Molecular Weight and Conversions for Methyl Methacrylate Polymerizations Carried Out in the Presence of Chain Transfer Agents (CTA)

| Entry | CTA | Temp. (°C.) | Time (hr.) | $10^3$[CTA]/ [Monomer] | % Conv. | $M_n$# |
|---|---|---|---|---|---|---|
| 1 | Ia | 60 | 1.00 | 0.00 | 15.80 | 327160 |
| 2 | Ia | 60 | 1.00 | 10.20 | 14.70 | 287300 |
| 3 | Ia | 60 | 1.00 | 22.80 | 13.30 | 253630 |
| 4 | Ib | 60 | 1.00 | 0.00 | 14.95 | 159200 |
| 5 | Ib | 60 | 1.00 | 16.80 | 13.35 | 104100 |
| 6 | Ib | 60 | 1.00 | 31.30 | 12.80 | 89900 |
| 7 | Ib | 60 | 1.00 | 68.30 | 11.20 | 58700 |
| 8 | Ic | 60 | 1.00 | 0.00 | 16.30 | 254350 |
| 9 | Ic | 60 | 1.00 | 14.32 | 12.10 | 195900 |
| 10 | Ic | 60 | 1.00 | 28.37 | 9.95 | 190150 |
| 11 | Ic | 60 | 1.00 | 56.73 | 8.30 | 153150 |
| 12 | If | 60 | 1.00 | 0.00 | 14.72 | 266800 |
| 13 | If | 60 | 1.00 | 9.82 | 2.44 | 89000 |
| 14 | If | 60 | 1.00 | 19.64 | 1.30 | 64875 |
| 15 | If | 60 | 1.00 | 38.58 | 1.22 | 50800 |
| 16 | Ig | 60 | 1.00 | 0.00 | 11.49 | 299000 |
| 17 | Ig | 60 | 1.00 | 9.89 | 4.48 | 113400 |
| 18 | Ig | 60 | 1.00 | 19.03 | 0.42 | 91990 |
| 19 | Ig | 60 | 1.00 | 36.34 | 1.47 | 57530 |
| 20 | Ii | 60 | 1.00 | 0.00 | 12.74 | 248860 |
| 21 | Ii | 60 | 1.00 | 9.89 | 11.52 | 131020 |
| 22 | Ii | 60 | 1.00 | 18.15 | 11.61 | 100900 |
| 23 | Ii | 60 | 1.00 | 34.50 | 10.30 | 71120 |

Number-average molecular weight determined by GPC, calibrated with polystyrene standards.

EXAMPLE 2

Polymerization of Styrene

Polymerizations of styrene (Sty) were carried out similarly for three hours at 60° C. $\alpha,\alpha'$-Azobisisobutyronitrile (21.6 mg) was dissolved in freshly distilled styrene (50 mL). Aliquots (10 mL) were removed and transferred to ampoules containing weighed amounts of chain transfer agent. After the degassing and polymerization, the contents of ampoules were poured into methanol and the precipitated polymers were collected, dried, and examined as before.

TABLE 2

Molecular Weight and Conversions for Styrene Polymerizations Carried Out in the Presence of Allylic Malonate Chain Transfer Agents and MMA Dimer (Methyl 4-methoxycarbonyl-2,2-dimethyl-4-pentenoate)

| Entry | CTA | Temp. (°C.) | Time (hr.) | $10^3$[CTA]/ [Monomer] | % Conv. | $M_n$# |
|---|---|---|---|---|---|---|
| 1 | Ia | 60 | 3.00 | 0.00 | 9.80 | 130000 |
| 2 | Ia | 60 | 3.00 | 13.20 | 8.40 | 119250 |
| 3 | Ia | 60 | 3.00 | 26.20 | 9.30 | 114300 |
| 4 | Ib | 60 | 3.00 | 0.00 | 8.30 | 127000 |
| 5 | Ib | 60 | 3.00 | 14.86 | 4.20 | 20400 |
| 6 | Ib | 60 | 3.00 | 32.78 | 3.65 | 12500 |
| 7 | Ib | 60 | 3.00 | 43.11 | 3.20 | 11400 |
| 8 | Ih | 60 | 3.00 | 0.00 | 8.4 | 103995 |
| 9 | Ih | 60 | 3.00 | 8.75 | 6.3 | 43755 |
| 10 | Ih | 60 | 3.00 | 16.90 | 5.8 | 28222 |
| 11 | Ih | 60 | 3.00 | 30.40 | 5.2 | 18682 |
| 12 | Ii | 60 | 3.00 | 0.00 | 9.0 | 112525 |
| 13 | Ii | 60 | 3.00 | 9.01 | 8.3 | 102660 |
| 14 | Ii | 60 | 3.00 | 18.35 | 7.4 | 89260 |
| 15 | Ii | 60 | 3.00 | 38.69 | 6.5 | 80940 |
| 16 | MMA Dimer | 60 | 3.00 | 0.00 | 10.5 | 120010 |
| 17 | MMA Dimer | 60 | 3.00 | 12.50 | 7.0 | 59855 |

TABLE 2-continued

Molecular Weight and Conversions for Styrene Polymerizations Carried Out in the Presence of Allylic Malonate Chain Transfer Agents and MMA Dimer (Methyl 4-methoxycarbonyl-2,2-dimethyl-4-pentenoate)

| Entry | CTA | Temp. (°C.) | Time (hr.) | $10^3$[CTA]/ [Monomer] | % Conv. | $M_n$# |
|---|---|---|---|---|---|---|
| 18 | MMA Dimer | 60 | 3.00 | 25.00 | 5.8 | 41220 |
| 19 | MMA Dimer | 60 | 3.00 | 49.88 | 5.7 | 27830 |

Number-average molecular weight determined by GPC, calibrated with polystyrene standards.

EXAMPLE 3

Polymerization of Acrylate Esters

Polymerizations of methyl acrylate (MA) (or ethyl acrylate, EA) were carried out using a stock solution prepared from α,α'-azobisisobutyronitrile (6.34 mg) and distilled thiophene-free benzene (25 mL). Aliquots (6 ml) were removed and added to ampoules containing freshly distilled methyl acrylate (4 mL), thiophene-free benzene (10 mL) and weighed amounts of the activated allylic malonate chain transfer agents. After degassing, the mixtures were polymerized at 60° C. for one hour; or at 80° C. for 30 minutes; or at 90° C. for 30 minutes. The volatiles were then removed on rotary evaporator and the polymers were dried in vacuo to constant weight and examined by GPC.

TABLE 3

Molecular Weight and Conversions for Acrylate Polymerizations Carried Out in the Presence of Chain Transfer Agents (CTA)

| Entry | Monomer | CTA | Temp. (°C.) | Time (hr.) | $10^3$[CTA]/ [Monomer] | % Conv. | $M_n$# |
|---|---|---|---|---|---|---|---|
| 1 | MA | Ia | 80 | 0.50 | 0.00 | 38.70 | 183900 |
| 2 | MA | Ia | 80 | 0.50 | 10.00 | 36.60 | 137500 |
| 3 | MA | Ia | 80 | 0.50 | 20.60 | 31.90 | 95750 |
| 4 | MA | Ia | 80 | 0.50 | 39.75 | 25.60 | 67400 |
| 5 | EA | Ib | 60 | 1.00 | 0.00 | 8.80 | 235,600 |
| 6 | EA | Ib | 60 | 1.00 | 4.33 | 4.60 | 89400 |
| 7 | EA | Ib | 60 | 1.00 | 5.87 | 3.85 | 53100 |
| 8 | EA | Ib | 60 | 1.00 | 12.81 | 2.30 | 33500 |
| 9 | MA | Ie | 60 | 1.00 | 0.00 | 26.3 | 493150 |
| 10 | MA | Ie | 60 | 1.00 | 3.73 | 25.3 | 467300 |
| 11 | MA | Ie | 60 | 1.00 | 14.67 | 21.8 | 362400 |
| 12 | MA | If | 60 | 1.00 | 0.00 | 28.2 | 388450 |
| 13 | MA | If | 60 | 1.00 | 9.43 | ~0.0 | 31455 |
| 14 | MA | If | 60 | 1.00 | 20.61 | ~0.0 | 8140 |
| 15 | MA | If | 60 | 1.00 | 34.18 | ~0.0 | 5810 |
| 16 | MA | If | 80 | 0.50 | 0.00 | 46.0 | 133300 |
| 17 | MA | If | 80 | 0.50 | 8.70 | 0.39 | 22630 |
| 18 | MA | If | 80 | 0.50 | 18.10 | 1.60 | 11540 |
| 19 | MA | If | 80 | 0.50 | 34.44 | ~0.0 | 4375 |
| 20 | MA | Ig | 60 | 1.00 | 0.00 | 21.44 | 657800 |
| 21 | MA | Ig | 60 | 1.00 | 8.84 | 0.47 | 13260 |
| 22 | MA | Ig | 60 | 1.00 | 21.32 | 0.14 | 4885 |
| 23 | MA | Ig | 60 | 1.00 | 37.33 | 0.0 | 3495 |
| 24 | MA | Ig | 80 | 0.50 | 0.00 | 17.36 | 187500 |
| 25 | MA | Ig | 80 | 0.50 | 9.43 | 0.30 | 7960 |
| 26 | MA | Ig | 80 | 0.50 | 20.73 | 0.21 | 3860 |
| 27 | MA | Ig | 80 | 0.50 | 38.79 | 0.12 | 2560 |
| 28 | MA | Ih | 60 | 1.00 | 0.00 | 20.5 | 926632 |
| 29 | MA | Ih | 60 | 1.00 | 6.54 | 22.6 | 66231 |
| 30 | MA | Ih | 60 | 1.00 | 13.30 | 27.5 | 37180 |
| 31 | MA | Ih | 60 | 1.00 | 26.50 | 12.9 | 21243 |
| 32 | MA | Ih | 80 | 0.50 | 0.00 | 40.6 | 176925 |
| 33 | MA | Ih | 80 | 0.50 | 6.91 | 38.3 | 48525 |
| 34 | MA | Ih | 80 | 0.50 | 13.30 | 32.1 | 26285 |
| 35 | MA | Ih | 80 | 0.50 | 26.50 | 28.4 | 16074 |
| 36 | MA | Ii | 60 | 1.00 | 0.00 | 23.4 | 739090 |
| 37 | MA | Ii | 60 | 1.00 | 7.49 | 3.2 | 151740 |
| 38 | MA | Ii | 60 | 1.00 | 14.29 | 1.7 | 98120 |
| 39 | MA | Ii | 60 | 1.00 | 29.24 | 0.2 | 52940 |
| 40 | MA | Ii | 90 | 0.50 | 0.00 | 55.6 | 83145 |
| 41 | MA | Ii | 90 | 0.50 | 6.93 | 20.9 | 46055 |
| 42 | MA | Ii | 90 | 0.50 | 14.91 | 16.4 | 28680 |
| 43 | MA | Ii | 90 | 0.50 | 28.99 | 14.9 | 18100 |

Number-average molecular weight determined by GPC, calibrated with polystyrene standards.

EXAMPLE 4

Polymerization of Vinyl Acetate

Polymerizations of vinyl acetate (VAc) were carried out in vacuo at 60° C. for one hour or at 80° C. for one hour using the following procedure. α,α'-Azobisisobutyronitrile (20.5 mg) was dissolved in freshly distilled vinyl acetate (25 mL). Aliquots (4 mL) were removed and added to ampoules containing weighed amounts of the chain transfer agents. After the polymerization, the volatiles were removed and the polymers were dried and examined as before.

TABLE 4

Molecular Weights and Conversions for Vinyl Acetate Polymerizations Carried Out in the Presence of Chain Transfer Agents (CTA)

| Entry | CTA | Temp. (°C.) | Time (hr.) | $10^3$[CTA]/ [Monomer] | % Conv. | $M_n$# |
|---|---|---|---|---|---|---|
| 1 | Ie | 80 | 1.00 | 0.00 | 60.2 | 62700 |
| 2 | Ie | 80 | 1.00 | 1.87 | 29.9 | 54700 |
| 3 | Ie | 80 | 1.00 | 3.72 | 18.9 | 38300 |
| 4 | Ie | 80 | 1.00 | 7.43 | 12.6 | 25900 |
| 5 | Ig | 60 | 1.00 | 0.00 | 5.37 | 193500 |
| 6 | Ig | 60 | 1.00 | 12.90 | 0.08 | 8200 |
| 7 | Ig | 60 | 1.00 | 23.90 | 0.02 | 5740 |
| 8 | Ig | 60 | 1.00 | 39.10 | 0.03 | 3260 |

Polystyrene standard equivalent number-average molecular weight.

Table 5 summarizes the results of chain transfer constants in polymerizations of common monomers using the allylic chain transfer agents [(Ia), (Ib), (Ic), (Ie), (If), (Ig) and (Ih)].

TABLE 5

Chain Transfer Constants ($C_x$) for Polymerizations of Common Monomers in the Presence of Allylic Transfer Agents and MMA Dimer

| CTA | Monomer | Conditions | Chain Transfer Constants ($C_x$) |
|---|---|---|---|
| Ia | MMA | 60° C. | 0.004 |
|  | MA | 80° C. | 0.020 |
|  | Sty | 60° C. | 0.004 |
| Ib | MMA | 60° C. | 0.015 |
|  | Sty | 60° C. | 0.148 |
|  | EA | 60° C. | 0.203 |
| MMA Dimer | EMA | 60° C. | 0.007 |
|  | EA | 60° C. | 0.120 |
|  | Sty | 60° C. | 0.057 |
| Ic | MMA | 60° C. | 0.004 |
| Ie | VAc | 80° C. | 0.274 |
|  | MA | 60° C. | 0.005 |
| If | MMA | 60° C. | 0.060 |
|  | MA | 60° C. | 0.450 |
|  | MA | 80° C. | 0.560 |

TABLE 5-continued

Chain Transfer Constants ($C_x$) for Polymerizations of Common Monomers in the Presence of Allylic Transfer Agents and MMA Dimer

| CTA | Monomer | Conditions | Chain Transfer Constants ($C_x$) |
|---|---|---|---|
| Ig | MMA | 60° C. | 0.040 |
| | MA | 60° C. | 0.670 |
| | MA | 80° C. | 0.850 |
| | VAc | 60° C. | 7.010 |
| Ih | MA | 60° C. | 0.150 |
| | MA | 80° C. | 0.180 |
| | Sty | 60° C. | 0.150 |
| Ii | MMA | 60° C. | 0.029 |
| | MA | 60° C. | 0.053 |
| | MA | 90° C. | 0.130 |
| | Sty | 60° C. | 0.009 |

EXAMPLE 5

Polymerization of Styrene

A multi-necked reactor was equipped with a stirrer, thermocouple, and condensor. The reactor was held under nitrogen positive pressure and the following ingredients were used.

| Part 1 | |
|---|---|
| Styrene | 2 ml |
| MEK | 4 ml |
| Transfer agent (Ib) | 370 mg |
| Part 2 | |
| Styrene | 8 ml |
| MEK | 12 ml |
| Part 3 | |
| AIBN | 14 mg |
| MEK | 2 ml |
| Part 4 | |
| MEK | 2 ml |

Part 1 was charged to the reactor and heated to 80° C. When the temperature stabilized at 80° C., part 2 (the monomer feed) was charged to the reactor concurrently with part 3 (the initiator feed) over 90 minutes via a syringe pump. Then part 4 was charged to the reactor as a single shot feed to rinse the syringe pump and the reaction mixture was held at 80° C. for further 120 minutes. The solvent and unreacted monomer were then distilled off. The result is summarized in Table 6.

TABLE 6

| | CTA(Ib) | $M_n$ | $M_w$ | Dispersity |
|---|---|---|---|---|
| Control | 0 | 20400 | 39350 | 1.93 |
| Example 5 | 370 mg | 14900 | 29600 | 1.94 |

EXAMPLES 6–8

Polymerization of n-Butyl Methacrylate/Hydroxypropyl Acrylate

A multi-necked reactor was equipped with a stirrer, thermocouple, and condensor. The reactor was held under nitrogen positive pressure and following ingredients were used in three separate polymerizations.

| PART | INGREDIENTS | Example 6 | Example 7 | Example 8 |
|---|---|---|---|---|
| I. | Xylene | 20.94 g | 20.94 g | 20.94 g |
| | Transfer Agent Ib | 0.00 g | 3.47 g | 6.94 g |
| II. | n-BMA | 51.17 g | 47.70 g | 44.23 g |
| | HPA | 18.23 g | 18.23 g | 18.23 g |
| III. | Xylene | 9.07 g | 9.07 g | 9.07 g |
| | VAZO 67 | 0.60 g | 0.60 g | 0.60 g |

Part I was charged to the reactor and heated to 90° C. When the temperature stabilized, Part II was charged to the reactor concurrently with Part III over 240 and 260 minutes, respectively. The reaction mixture was held for 60 minutes following the completion of the feeding of Part III. The monomer conversion was determined by solids analysis and molecular weight was determined by GPC. The results are summarized in Table 7.

TABLE 7

| Example Number | Wt % CTA(Ib) | Mn | Mw | Dispersity | Conversion |
|---|---|---|---|---|---|
| 6 | 0 (control) | 27180 | 65950 | 2.43 | 100% |
| 7 | 5.0% | 16410 | 37940 | 2.31 | 98% |
| 8 | 10.0% | 12730 | 26750 | 2.10 | 100% |

We claim:

1. A process for the free radical initiated polymerization of ethylenically unsaturated monomer species characterised by the use of compounds of Formula (I) as chain transfer agents.

Formula (I)

wherein

X is selected from hydrogen; CN; optionally substituted aryl; COOH; COOR; C(O)NHR$^6$; C(O)NR$^7$R$^8$; and halogen;

Q is selected from COOR$^1$; CN; and C(O)NR$^7$R$^8$;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN and optionally substituted aryl; $C_1$ to $C_6$ alkenyl; and $C_1$ to $C_6$ alkynyl;

Z is selected from COOR$^2$; CN; and optionally substituted aryl;

R$^3$ and R$^4$ may be the same or different and are selected from hydrogen, $C_1$ to $C_4$ alkyl and halogen; or R$^3$ and R$^4$ together with the carbon atom to which they are attached form part of a carbocyclic or heterocyclic ring structure;

R is selected from $C_1$ to $C_{18}$ alkyl; $C_1$ to $C_{12}$ alkyl substituted with one or more substituents selected from hydroxy, amino, $C_1$ to $C_6$ alkoxy, phenyl, halogen, NCO, CN, and COOR$^5$;

R$^1$ and R$^2$ may be the same or different and are selected from $C_1$ to $C_{18}$ alkyl; $C_1$ to $C_{12}$ alkyl substituted with one or more substituents selected from hydroxy, $C_1$ to $C_6$ acyloxy, $C_1$ to $C_6$ alkoxy, amino, halogen, Si(R$^9$)$_3$, Si(OR$^9$)$_3$, optionally substituted aryl, CN and NCO;

R$^5$ is selected from hydrogen and $C_1$ to $C_6$ alkyl;

$R^6$ is selected from hydrogen and $C_1$ to $C_{18}$ alkyl;

$R^7$ and $R^8$ may be the same or different and are selected from $C_1$ to $C_{18}$ alkyl; and $R^9$ is selected from $C_1$ to $C_{18}$ alkyl; $C_1$ to $C_{18}$ cycloalkyl; and optionally substituted aryl.

2. The process of claim 1 wherein X is a phenyl, substituted phenyl, chloro or bromo group.

3. The process of claim 1 wherein Y is a phenyl or substituted phenyl.

4. The process of claim 1 wherein $R^3$ and $R^4$ may be the same or different and are a chloro or fluoro group.

5. The process of claim 1 wherein compounds of Formula (LA) are used as chain transfer agents.

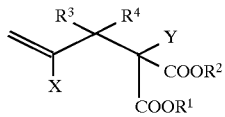
Formula (IA)

wherein

Y, R, $R^6$, $R^7$ and $R^8$ are as defined in claim 1;

X is selected from hydrogen; CN; optionally substituted aryl; COOH; COOR; $C(O)NHR^6$; $C(O)NR^7R^8$; and halogen;

Y is selected from hydrogen; $C_1$ to $C_6$ alkyl; $C_1$ to $C_6$ alkyl substituted with one or more substituents selected from hydroxy, amino, $C_1$ to $C_6$ alkoxy, $C_1$ to $C_6$ alkoxycarbonyl, halogen, CN, optionally substituted aryl; $C_1$ to $C_6$ alkenyl; and $C_1$ to $C_6$ alkynyl;

$R^1$ and $R^2$ may be the same or different and are selected from $C_1$ to $C_{18}$ alkyl; $C_1$ to $C_{12}$ alkyl substituted with a substituent selected from hydroxy, $C_1$ to $C_6$ acyloxy, $C_1$ to $C_6$ alkoxy, amino, halogen, optionally substituted aryl, CN and NCO; and $R^3$ and $R^4$ may be the same or different and are selected from hydrogen; $C_1$ to $C_4$ alkyl; and halogen.

6. The process of claim 5 wherein X is a phenyl, substituted phenyl, chloro or bromo group.

7. The process of claim 5 wherein Y is a phenyl or substituted phenyl.

8. The process of claim 5 wherein $R^3$ and $R^4$ may be the same or different and are hydrogen, chloro or fluoro groups.

9. The process of claim 1 wherein compounds of Formula (IB) are used as chain transfer agents:

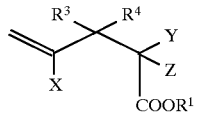
Formula (IB)

wherein

X, Y, $R^1$, $R^3$ and $R^4$ are as defined in claim 1; and

Z is optionally substituted aryl.

10. The process of claim 1 where the polymerisation occurs in solution.

11. The process of claim 1 where the polymerisation occurs in an emulsified phase.

12. The process of claim 1 when the unsaturated species are added before the polymerisation commences.

13. The process of claim 1 when the unsaturated species are added during the reaction.

14. The process of claim 1 when part of the unsaturated species are added before the start of the reaction and the remainder of the unsaturated species are added during the reaction.

15. A compound of Formula (I) as defined in claim 1 which is selected from:

ethyl 2,4-bis(ethoxycarbonyl)-2-methyl-4-pentenoate;

ethyl 2,4-bis(ethoxycarbonyl)-2-ethyl-4-pentenoate;

ethyl 2-benzyl-2,4-bis(ethoxycarbonyl)-4-pentenoate;

ethyl 2-ethoxycarbonyl-2-methyl-4-phenyl-4-pentenoate;

ethyl 2-ethoxycarbonyl-2,3-dimethyl-4-(t-butoxycarbonyl)-4-pentenoate; and ethyl 2-phenyl-4-(t-butoxycarbonyl)-4-pentenoate.

16. A compound of Formula (1) as defined in claim 1 for use as a chain transfer agent in the free radical initiated polymerisation of unsaturated species.

17. A chain transfer agent for use in the free radical initiated polymerisation of unsaturated species which comprises a compound of Formula (I) as defined in any one of claim 1.

* * * * *

UNITED STATES PATENT AND TRADEMARK OFFICE
CERTIFICATE OF CORRECTION

PATENT NO. : 5,773,543
DATED : June 30, 1998
INVENTOR(S) : Ezio Rizzardo et al.

It is certified that error appears in the above-identified patent and that said Letters Patent is hereby corrected as shown below:

Column 13, Claim 5, line 13, delete "(LA)" and substitute therefor -- (IA) --.

Column 14, Claim 17, line 40, delete "any one of".

Signed and Sealed this

Sixteenth Day of November, 1999

Attest:

Q. TODD DICKINSON

*Attesting Officer*      *Acting Commissioner of Patents and Trademarks*